United States Patent [19]

Diehr et al.

[11] Patent Number: 4,704,158

[45] Date of Patent: Nov. 3, 1987

[54] 1-(2-OXYAMINOCARBONYLPHENYLSUL-PHONYL)-3-HETEROARYL-UREAS

[75] Inventors: Hans-Joachim Diehr; Christa Fest, both of Wuppertal; Rolf Kirsten, Monheim; Joachim Kluth, Langenfeld; Klaus-Helmut Müller, Duesseldorf; Theodor Pfister, Monheim; Uwe Priesnitz, Solingen; Hans-Jochem Riebel, Wuppertal; Wolfgang Roy, Langenfeld; Hans-Joachim Santel, Cologne; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 769,225

[22] Filed: Aug. 23, 1985

[30] Foreign Application Priority Data

Aug. 30, 1984 [DE] Fed. Rep. of Germany ....... 3531927
May 8, 1985 [DE] Fed. Rep. of Germany ....... 3516435

[51] Int. Cl.[4] .................... C07D 239/69; A01N 43/54
[52] U.S. Cl. ........................................ 71/92; 544/321; 544/323; 544/332
[58] Field of Search .................... 71/92; 544/321, 323, 544/332

[56] References Cited

U.S. PATENT DOCUMENTS 4,555,261 11/1985 Petersen .................................. 71/93

Primary Examiner—John M. Ford
Attorney, Agent, or Firm—Sprung Horn Kramer & Woods

[57] ABSTRACT

The invention relates to new 1-(2-oxyaminocarbonyl-phenylsulphonyl)-3-heteroaryl-ureas of the general formula (I)

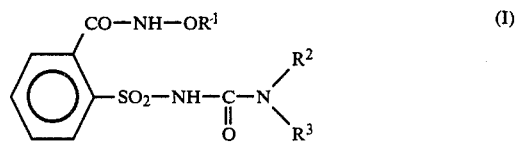

in which
- $R^1$ represents an optionally substituted radical from the series comprising alkyl, alkenyl, alkinyl, cycloalkyl, cycloalkylalkyl, aralkyl and aryl,
- $R^2$ represents hydrogen or an optionally substituted radical from the series comprising alkyl, alkenyl, alkinyl and aralkyl and
- $R^3$ represents an optionally substituted and/or optionally fused six-membered aromatic heterocyclic radical which contains at least one nitrogen atom, a process for their preparation, and their use as herbicides.

6 Claims, No Drawings

1-(2-OXYAMINOCARBONYLPHENYLSULPHONYL)-3-HETEROARYL-UREAS

The invention relates to new 1-(2-oxyaminocarbonylphenylsulphonyl)-3-heteroaryl-ureas, an inventive process for their preparation and their use as herbicides.

It is known that certain 1-arylsulphonyl-3-heteroaryl-ureas, such as, for example, 1-(2-methoxyphenylsulphonyl)-3-(4,6-dimethyl-pyrimidin-2-yl)-urea, have a herbicidal action. However, the action of these compounds is not always completely satisfactory (compare U.S. Pat. No. 4,169,719).

New 1-(2-oxyaminocarbonylphenylsulphonyl)-3-heteroaryl-ureas of the general formula (I)

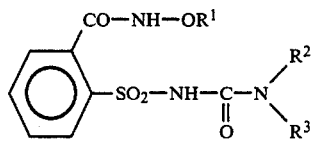

in which
R$^1$ represents an optionally substituted radical from the series comprising alkyl, alkenyl, alkinyl, cycloalkyl, cycloalkylalkyl, aralkyl and aryl,
R$^2$ represents hydrogen or an optionally substituted radical from the series comprising alkyl, alkenyl, alkinyl and aralkyl and
R$^3$ represents an optionally substituted and/or optionally fused six-membered aromatic heterocyclic radical which contains at least one nitrogen atom,
have now been found.

The new compounds of the formula (I) are obtained by an inventive process in which heterocyclic compounds of the formula (II)

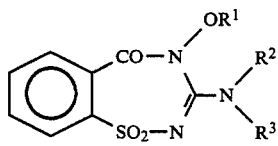

in which
R$^1$, R$^2$ and R$^3$ have the abovementioned meanings,
are reacted with water in the presence of mineral acids and if appropriate in the presence of diluents, at temperatures between 0° C. and 100° C.

The new 1-(2-oxyaminocarbonylphenylsulphonyl)-3-heteroaryl-ureas of the formula (I) are distinguished by a powerful herbicidal activity.

Surprisingly, the new compounds of the formula (I) exhibit a considerably better herbicidal action than many known chemical compounds of the same type of action.

It is also to be regarded as surprising that the compounds of the formula (I) according to the invention can be prepared by selective ring-opening of heterocyclic compounds of the formula (II), since other ring-opening reactions, for example by attack on the carbonyl or on the sulphonyl grouping, were to be expected, in addition to this novel reaction.

The invention preferably relates to compounds of the formula (I) in which
R$^1$ represents C$_1$-C$_{12}$-alkyl [which is optionally substituted by fluorine, chlorine, cyano, C$_1$-C$_4$-alkoxy, C$_1$-C$_4$-alkylthio, C$_1$-C$_4$-alkylsulphinyl, C$_1$-C$_4$-alkylsulphonyl, C$_1$-C$_4$-alkyl-carbonyl, C$_1$-C$_4$-alkoxy-carbonyl, C$_1$-C$_4$-alkylamino-carbonyl or di-(C$_1$-C$_4$-alkyl)-amino-carbonyl], or represents C$_3$-C$_6$-alkenyl [which is optionally substituted by fluorine, chlorine or bromine], C$_3$-C$_6$-alkinyl, C$_3$-C$_6$-cycloalkyl, C$_3$-C$_6$-cycloalkyl-C$_1$-C$_2$-alkyl or phenyl-C$_1$-C$_2$-alkyl [which is optionally substituted by fluorine, chlorine, nitro, cyano, C$_1$-C$_4$-alkyl, C$_1$-C$_4$-alkoxy or C$_1$-C$_4$-alkoxycarbonyl], or represents benzhydryl, or represents phenyl [which is optionally substituted by fluorine, chlorine, nitro, cyano, C$_1$-C$_4$-alkyl, trifluoromethyl, C$_1$-C$_4$-alkoxy, C$_1$-C$_2$-fluoroalkoxy, C$_1$-C$_4$-alkylthio, trifluoromethylthio or C$_1$-C$_4$-alkoxycarbonyl], and in which, furthermore,
R$^2$ represents hydrogen or C$_1$-C$_4$-alkyl [which is optionally substituted by fluorine, chlorine, cyano, C$_1$-C$_4$-alkoxy, C$_1$-C$_4$-alkylthio, C$_1$-C$_4$-alkylsulphinyl, C$_1$-C$_4$-alkylsulphonyl, C$_1$-C$_4$-alkyl-carbonyl, C$_1$-C$_4$-alkoxy-carbonyl, C$_1$-C$_4$-alkylamino-carbonyl or di-(C$_1$-C$_4$-alkyl)-aminocarbonyl], or represents C$_3$-C$_6$-alkenyl, C$_3$-C$_6$-alkinyl or phenyl-C$_1$-C$_2$-alkyl [which is optionally substituted by fluorine, chlorine, nitro, cyano, C$_1$-C$_4$-alkyl, C$_1$-C$_4$-alkoxy or C$_1$-C$_4$-alkoxycarbonyl], and in which, furthermore,
R$^3$ represents the radical

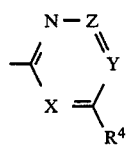

wherein
R$^4$ represents hydrogen, fluorine, chlorine, bromine, hydroxyl, C$_1$-C$_4$-alkyl [which is optionally substituted by fluorine and/or chlorine], C$_1$-C$_4$-alkoxy [which is optionally substituted by fluorine and/or chlorine], C$_1$-C$_4$-alkylthio [which is optionally substituted by fluorine and/or chlorine], amino, C$_1$-C$_4$-alkylamino or di-(C$_1$-C$_4$-alkyl)-amino,
X represents nitrogen or a methine bridge (CH),
Y represents nitrogen or an optionally substituted methine bridge C—R$^5$,
wherein
R$^5$ represents hydrogen, fluorine, chlorine, bromine, cyano, formyl or C$_1$-C$_4$-alkyl [which is optionally substituted by fluorine and/or chlorine], or represents C$_1$-C$_4$-alkyl-carbonyl or C$_1$-C$_4$-alkoxy-carbonyl, and
Z represents nitrogen or an optionally substituted methine bridge C—R$^6$,
wherein
R$^6$ represents hydrogen, fluorine, chlorine, bromine, hydroxyl, C$_1$-C$_4$-alkyl [which is optionally substituted by fluorine and/or chlorine], C$_1$-C$_4$-alkoxy [which is optionally substituted by fluorine and/or chlorine], C$_1$-C$_4$-alkylthio [which is optionally substituted by fluorine and/or chlorine], amino, C$_1$-C$_4$-alkylamino or di-(C$_1$-C$_4$-alkyl)-amino.

The invention particularly relates to compounds of the formula (I) in which
R$^1$ represents C$_1$-C$_8$-alkyl [which is optionally substituted by fluorine or chlorine], C$_3$-C$_4$-alkenyl, $C_1$-$C_2$-alkoxy-carbonylmethyl, phenyl, phenethyl or benzyl [which is optionally substituted by fluorine, chlorine, nitro, cyano, methyl, methoxy or methoxy-carbonyl], $R^2$ represents hydrogen and $R^3$ represents the radical

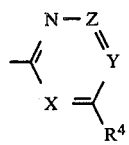

wherein $R^4$ represents chlorine, methyl, ethyl, methoxy, difluoromethoxy or ethoxy, X represents nitrogen, Y represents a methine bridge (CH) and Z represents an optionally substituted methine bridge C—$R^6$, wherein $R^6$ represents hydrogen, chlorine, methyl, methoxy, ethoxy, methylthio, ethylthio, dimethylamino or diethylamino.

The chemical reaction which proceeds in the process according to the invention can be outlined, for example, by the following equation:

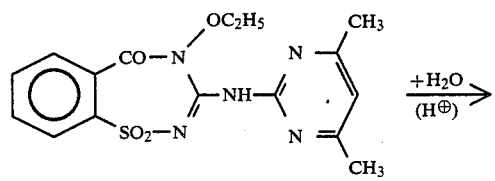

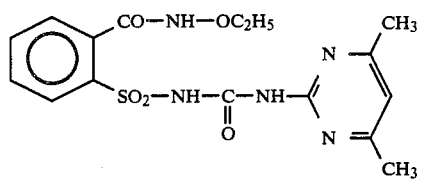

Formula (II) provides a general definition of the heterocyclic compounds to be used as starting compounds in the process according to the invention.

In formula (II), $R^1$, $R^2$ and $R^3$ preferably and particularly have the same meanings as are given above as preferred or as particularly preferred in the context of the definition of the substituents of formula (I).

Examples of starting substances of the formula (II) are listed in the following Table 1.

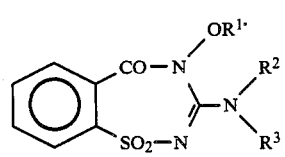

TABLE 1

Examples of starting substances of the formula (II)

| $R^1$ | $R^2$ | $R^3$ |
|---|---|---|
| $CH_3$ | H | ![pyrimidine with CH3, CH3] |
| $CH_3$ | $CH_3$ | ![pyrimidine with CH3, CH3] |
| $C_2H_5$ | H | ![pyrimidine with CH3, CH3] |
| $C_2H_5$ | $CH_3$ | ![pyrimidine with CH3, CH3] |
| $C_3H_7$—n | H | ![pyrimidine with CH3, CH3] |
| $C_3H_7$—n | $CH_3$ | ![pyrimidine with CH3, CH3] |
| $C_3H_7$—iso | H | ![pyrimidine with CH3, CH3] |
| $C_3H_7$—iso | $CH_3$ | ![pyrimidine with CH3, CH3] |

TABLE 1-continued

Examples of starting substances of the formula (II)

| R¹ | R² | R³ |
|---|---|---|
| C₄H₉—n | H | 4,6-dimethylpyrimidin-2-yl |
| C₄H₉—n | CH₃ | 4,6-dimethylpyrimidin-2-yl |
| C₄H₉—sec. | H | 4,6-dimethylpyrimidin-2-yl |
| C₄H₉—sec. | CH₃ | 4,6-dimethylpyrimidin-2-yl |
| C₄H₉—iso | H | 4,6-dimethylpyrimidin-2-yl |
| C₄H₉—iso | CH₃ | 4,6-dimethylpyrimidin-2-yl |
| C₈H₁₇—n | H | 4,6-dimethylpyrimidin-2-yl |
| C₈H₁₇—n | CH₃ | 4,6-dimethylpyrimidin-2-yl |
| —CH₂—C₆H₅ | H | 4,6-dimethylpyrimidin-2-yl |
| —CH₂—C₆H₅ | CH₃ | 4,6-dimethylpyrimidin-2-yl |
| —CH₂CH₂—C₆H₅ | H | 4,6-dimethylpyrimidin-2-yl |
| —CH₂CH₂—C₆H₅ | CH₃ | 4,6-dimethylpyrimidin-2-yl |
| —CH₂—C₆H₄—CH₃ (p) | H | 4,6-dimethylpyrimidin-2-yl |
| —CH₂—C₆H₄—CH₃ (p) | CH₃ | 4,6-dimethylpyrimidin-2-yl |
| —CH₂—C₆H₄—Cl (o) | H | 4,6-dimethylpyrimidin-2-yl |
| —CH₂—C₆H₄—Cl (o) | CH₃ | 4,6-dimethylpyrimidin-2-yl |

TABLE 1-continued

| Examples of starting substances of the formula (II) | | |
|---|---|---|
| $R^1$ | $R^2$ | $R^3$ |
|  | H |  |

The compounds of the formula (II) have not yet been described in the literature. The compounds of the formula (II) are obtained by a process in which 2-chlorosulphonylbenzoyl chloride of the formula (III)

 (III)

is reacted with oxyguanidine derivatives of the formula (IV)

 (IV)

in which $R^1$, $R^2$ and $R^3$ have the abovementioned meaning, in the presence of acid acceptors, such as, for example, pyridine or diazabicyclooctane (DABCO), and, if appropriate, in the presence of diluents, such as, for example, methylene chloride, chloroform, tetrahydrofuran or dioxane, at temperatures between $-30°$ C. and $+50°$ C.

The mixture can be worked up by customary methods, for example by concentrating, taking up the residue in methylene chloride, washing the mixture with dilute hydrochloric acid and with water and separating off, drying, filtering and concentrating the organic phase, the products of the formula (II) remaining in the residue.

The 2-chlorosulphonylbenzoyl chloride of the formula (III) to be used as the starting substance is already known (compare DE-OS (German Published Specification) No. 2,036,171).

Formula (IV) provides a general definition of the oxyguanidine derivatives also to be used as starting substances. In formula (IV), $R^1$, $R^2$ and $R^3$ preferably and particularly have the same meanings as are given above as preferred or as particularly preferred in the context of the definition of the substituents of the formula (I).

Examples which may be mentioned of starting substances of the formula (IV) are: N'-(4-methyl-pyrimidin-2-yl)-, N'-(4-ethyl-pyrimidin-2-yl)-, N'-(4,6-dimethoxypyrimidin-2-yl)-, N'-(4,6-diethoxy-pyrimidin-2-yl)-, N'-(4-difluoromethoxy-6-methyl-pyrimidin-2-yl)-, N'-(4,6-dimethyl-pyrimidin-2-yl)-, N'-(4-methoxy-6-methyl-pyrimidin-2-yl)-, N'-(4-ethoxy-6-methyl-pyrimidin-2-yl)-, N'-(4-choro-6-methoxy-pyrimidin-2-yl)-, N'-(4-chloro-6-ethoxy-pyrimidin-2-yl)-, N'-(4-chloro-6-dimethylamino-pyrimidin-2-yl)-, N'-(4-methyl-6-methylthio-pyrimidin-2-yl)- and N'-(4-dimethylamino-6-methyl-pyrimidin-2-yl)-N''-methoxy-guanidine, -N''-ethoxy-guanidine, -N''-propoxy-guanidine, -N''-isopropoxyguanidine, -N''-butoxy-guanidine, -N''-isobutoxy-guanidine, -N''-sec.-butoxy-guanidine, -N''-pentoxy-guanidine, -N''-isopentoxy-guanidine, -N''-hexyloxy-guanidine, -N''-octyloxy-guanidine, -N''-allyloxy-guanidine, -N''-(2-chloro-ethoxy)-guanidine, -N''-(2-fluoro-ethoxy)-guanidine, -N''-(2-chloro-propoxy)-guanidine, -N''-(2-fluoro-propoxy)-guanidine, -N''-(3-chloro-propoxy)-guanidine, -N''-(4-chloro-butoxy)-guanidine, -N''-methoxycarbonylmethoxy-guanidine, -N''-ethoxycarbonylmethoxy-guanidine, -N''-(1-methoxycarbonyl-ethoxy)-guanidine, -N''-(1-ethoxycarbonylethoxy)-guanidine, -N''-dimethylaminocarbonylmethoxy-guanidine, -N''-(2-phenyl-ethoxy)-guanidine, -N''-phenoxy-guanidine, -N''-(4-methyl-benzyloxy)-guanidine, -N''-(4-fluoro-benzoyloxy)-guanidine, -N''-(4-chlorobenzyloxy)-guanidine, -N''-(4-nitrobenzoyloxy)-guanidine, -N''-(2,6-dichloro-benzoyloxy)-guanidine, -N''-(4-methoxycarbonyl-benzyloxy)-guanidine and -N''-(4-ethoxycarbonylbenzyloxy)-guanidine.

The starting substances of the formula (IV) are known in some cases (compare J. Chem. Soc. 1962, 3915 and DE-OS (German Published Specification) No. 3,334,455).

The compounds of the formula (IV) are obtained by a process in which cyanamide derivatives of the formula (V)

 (V)

in which $R^2$ and $R^3$ have the abovementioned meanings, are reacted with hydroxylamine derivatives of the formula (VI)

$H_2N-OR^1$ (VI)

in which $R^1$ has the abovementioned meanings, or with hydrochloride of hydroxylamine derivatives of the formula (VI), if appropriate in the presence of diluents, such as, for example, ethanol, propanol or butanol, at temperatures between 20° C. and 120° C. and, if appropriate, the reaction products are treated with acid acceptors, such as, for example, ammonia, potassium carbonate or sodium hydroxide.

The cyanamide derivatives of the formula (V) are known in some cases (compare J. Chem. Soc. 1953, 1725). The compounds of the formula (V) are essentially obtained by the following synthesis routes:

(a) by reaction of alkali metal or alkaline earth metal salts of cyanamide—such as, for example, sodium cyanamide or calcium cyanamide—with chloro-hetarenes of the formula (VII)

Cl—$R^3$ (VII)

in which $R^3$ has the abovementioned meaning, and, if appropriate, subsequently—if $R^2$ does not represent hydrogen—with halogen compounds of the formula (VIII)

$$Q-R^2 \quad (VIII)$$

in which
R² represents an optionally substituted radical from the series comprising alkyl, alkenyl, alkinyl and aralkyl and
Q represents chlorine, bromine or iodine,
if appropriate in the presence of inert diluents, such as, for example, acetone, acetonitrile or dimethylformamide, at temperatures between 0° C. and 100° C.

After the mixture has been concentrated and the residue has been dissolved in water, the cyanamide derivatives of the formula (V) can be precipitated by acidification, for example with hydrochloric acid, and isolated by filtration with suction.

Alternatively, the compounds of the formula (V) are obtained (b) in the case where R³ represents a substituted pyrimidinyl radical, by reaction of cyanoguanidine ("dicyanidiamide") with β-dicarbonyl compounds or derivatives thereof, such as acetylacetone (compare J. Chem. Soc. 1953, 1725–1730), acetoacetic acid esters (compare J. Prakt. Chem. 77 (1908), 542 and J. Chem. Soc. 1948, 586) or malonic acid esters (compare German patent specification No. 158,591).

The 2-cyanoamino-4-hydroxy-6-methyl- or -4,6-dihydroxy-pyrimidines obtained from acetoacetic acid esters of malonic acid esters can be converted into corresponding 2-cyanoamino-4-alkoxy-6-methyl- or 4,6-dialkoxy-pyrimidines in a known manner by reaction with alkylating agents, such as, for example, dimethyl sulphate or diethyl sulphate, if appropriate in the presence of diluents, such as, for example, water, methanol, ethanol, n- or iso-propanol, acetone, dioxane or dimethylformamide, and in the presence of acid-binding agents, such as, for example, sodium hydroxide or potassium hydroxide or sodium carbonate or potassium carbonate. To avoid N-alkylation, acylation is carried out, if appropriate, with an acylating agent, such as, for example, acetic anhydride or acetyl chloride, and, after the alkylation, the product is deacylated again with aqueous acids or bases.

In another alternative process, the compounds of the formula (V) are obtained by a process in which (c) amino-hetarenes of the formula (IX)

$$H_2N-R^3 \quad (IX)$$

in which
R³ has the above mentioned meaning,
are reacted with carbonyl isothiocyanates of the formula (X)

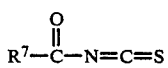

(X)

in which
k⁷ represents ethoxy or phenyl,
if appropriate in the presence of an inert diluent, such as, for example, acetone, acetonitrile or toluene, at temperatures between 0° C. and 100° C., the carbonylthioureas of the formula (XI) thereby formed

(XI)

in which

R³ and R⁷ have the abovementioned meanings,
are isolated by filtration with suction, if appropriate after concentration of the mixture, and are reacted with aqueous alkali metal or alkaline earth metal hydroxide solutions, such as, for example, sodium hydroxide solution, if appropriate in the presence of an organic solvent, such as, for example, tetrahydrofuran or dioxane, at temperatures between 0° C. and 120° C., and the thioureas obtained as crystals after acidification, for example with hydrochloric acid, of the formula (XII)

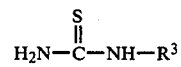

(XII)

in which
R³ has the abovementioned meaning,
are isolated by filtration with suction and reacted with metal compounds which can bond hydrogen sulphide, such as, for example, lead-II acetate, copper-II acetate, mercury-II acetate or iron-II acetate, in the presence of aqueous alkali metal or alkaline earth metal hydroxide solutions, such as, for example, sodium hydroxide solution, at temperatures between 20° C. and 100° C., and, when the reaction has ended, the mixture is filtered and the filtrate is acidified with an acid, such as, for example, acetic acid. The products of the formula (V) thereby obtained as crystals can be isolated by filtration with suction.

The starting substances for the preparation processes described above under (a), (b) and (c) for the cyanamide derivatives of the formula (V) are known and/or can be prepared by processes which are known per se.

These include the chloro-hetarenes of the formula (VII) (compare J. Chem. Soc. (c) 1966, 2031; Chem. Pharm. Bull. 11 (1963), 1382–1388 and Arch. Pharm. 295, (1962), 649–657), the halogen compounds of the formula (VII) (commercially available chemicals), the amino-hetarenes of the formula (IX) (compare Chem. Pharm. Bull. 11, (1963); J. Chem. Soc. 1946, 81 and U.S. Pat. No. 4,299,960) and the carbonyl isothiocyanates of the formula (X) (compare J. Heterocycl. Chem. 5, (1968), 837 and U.S. Pat. No. 4,160,037).

The process according to the invention for the preparation of the new compounds of the formula (I) is preferably carried out in water as the solvent. Other possible diluents are all the inert organic solvents, but preferably aprotic polar solvents. These include, where appropriate, ketones, such as, for example, acetone and methyl ethyl ketone, nitriles, such as, for example, acetonitrile and propionitrile, dimethylsulphoxide, sulpholane and 1,2-dimethoxyethane.

The process according to the invention is carried out in the presence of mineral acids. Examples of these are hydrochloric acid, sulphuric acid and phosphoric acid. Hydrochloric acid is preferably used.

The reaction temperatures can be varied within a substantial range in the process according to the invention. In general, the reaction is carried out between 0° C. and +100° C., preferably between 10° C. and +50° C. The process according to the invention is in general carried out under normal pressure.

For carrying out the process according to the invention, in general between 1 and 25 moles, preferably between 1 and 10 moles, of hydrochloric acid are employed per mole of the heterocyclic compound of the formula (II).

The reaction compounds are usually brought together at room temperature and the reaction mixture is stirred until the reaction has ended.

The new compounds of the formula (I) can be worked up and isolated by customary methods. For example, the reaction mixture is concentrated when the reaction has ended. The product of the formula (I) which remains in the residue is made to crystallise by trituration with a suitable organic solvent, such as, for example, ethanol, and is isolated by filtration with suction.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galibsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dioctyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopercurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is now restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm lantations, cocoa plantations, soft fruit plantings and hopfields, and for the selective combating of weeds in annula cultures.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussion Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

For the mixture come known herbicides, such as, for example, N-(2-benzothiazolyl)-N,N'-dimethyl-urea, 3-(3-chloro-4-methylphenyl)-1,1-dimethylurea, 3-(4-isopropylphenyl)-1,1-dimethylurea, 4-amino-6-(1,1-dimethyl-ethyl)-3-methylthio-1,2,4-triazin-5(4H)-one, 4-amino-6-(1,1-dimethyl-ethyl)-3-ethylthio-1,2,4-triazin-5(4H)-one, 1-amino-6-ethylthio-3-(2,2-dimethylpropyl)-1,3,5-triazine-2,4-(1H,3H)-dione, 4-amino-3-methyl-6-phenyl-1,2,4-triazin-5(4H)-one, 2-chloro-4-ethylamino-6-isopropylamino-1,3,5-triazine, the R-enantiomer of (trimethylsilyl)-methyl 2-[4-(3,5- dichloropyridin-2-oxy)-phenoxy]-propionate, the R-enantiomer of (2-benzyloxy)-ethyl 2-[4-(3,5-dichloropyridyl-2-oxy)-phenoxy]-propionate, 2,4-dichlorophenoxyacetic acid, 2-(2,4-dichlorophenoxy)-propionic acid, 4-chloro-2-methyl-phenoxy-acetic acid, 2-(2-methyl-4-chloro-phenoxy)-propionic acid, 3,5-diiodo-4-hydroxy-benzonitrile, 3,5-dibromo-4-hydroxy-benzonitrile and diphenyl ethers and phenylpyridazines, such as, for example, pyridates. Surprisingly some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.001 and 15 kg of active compound per hectare of soil surface, preferably between 0.005 and 10 kg per ha.

The preparation and use of the active compounds according to the invention can be seen from the following examples.

PREPARATION EXAMPLES

EXAMPLE 1

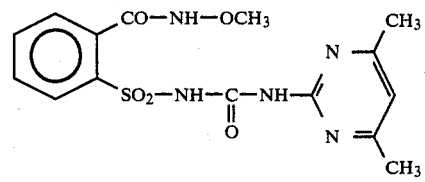

2.5 g (0.007 mole) of the heterocyclic compound of the following structural formula

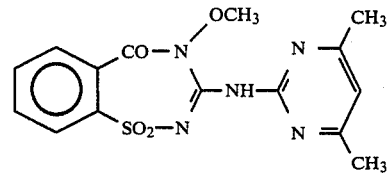

30 ml of water and 5 ml of concentrated hydrochloric acid are stirred at 20°–25° C. for 15 hours. This mixture is then evaporated and the residue is triturated with ethanol. The product thereby precipitated as crystals is isolated by filtration with suction.

0.8 g (30% of theory) of 1-(2-methoxyaminocarbonylphenylsulphonyl)-3-(4,6-dimethylpyrimidin-2-yl)urea of melting point 218° C. are obtained.

The compounds of the formula (I) listed in the following Table 2 can be prepared by the process described by way of example in the preceding example:

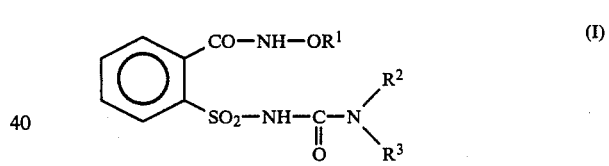

TABLE 2

| Example No. | $R^1$ | $R^2$ | $R^3$ | Melting point (°C.) |
|---|---|---|---|---|
| 2 | —$C_8H_{17}$—n | H | ![pyrimidine with 2 CH3] | 165 |
| 3 | —$C_4H_9$—n | H | ![pyrimidine with 2 CH3] | |
| 4 | —$CH_2$—Ph | H | ![pyrimidine with 2 CH3] | |

TABLE 2-continued

| Example No. | R¹ | R² | R³ | Melting point (°C.) |
|---|---|---|---|---|
| 5 | —C₂H₅ | H | pyrimidine with 4,6-diCH₃ | |
| 6 | —C₃H₇—n | H | pyrimidine with 4,6-diCH₃ | |
| 7 | —C₃H₇—i | H | pyrimidine with 4,6-diCH₃ | |
| 8 | —C₄H₉—i | H | pyrimidine with 4,6-diCH₃ | |
| 9 | —CH₂CH₂—C₆H₅ | H | pyrimidine with 4,6-diCH₃ | |
| 10 | —CH₂CH=CH₂ | H | pyrimidine with 4,6-diCH₃ | 177 (Decomposition) |
| 11 | —CH₃ | H | pyrimidine with 4-CH₃, 6-OCH₃ | 173 |
| 12 | —CH₃ | H | pyrimidine with 4,6-diOCH₃ | |

TABLE 2-continued

| Example No. | R¹ | R² | R³ | Melting point (°C.) |
|---|---|---|---|---|
| 13 | —CH₂CH(CH₃)₂ | H | 2-methyl-4-methyl-6-methoxypyrimidinyl | |
| 14 | —C₂H₅ | H | 2-methyl-4,6-dimethoxypyrimidinyl | |
| 15 | —CH₃ | H | 2-methyl-4-methyl-6-(OCHF₂)pyrimidinyl | |
| 16 | —CH₂—CH=CH₂ | H | 2-methyl-4-methylpyrimidinyl | |
| 17 | —CH₃ | H | 2-methyl-4-ethylpyrimidinyl | |
| 18 | —C₃H₇n | H | 2-methylpyrimidinyl | |
| 19 | —CH₂—COOC₂H₅ | H | 2-methyl-4-methylpyrimidinyl | |
| 20 | —CH₃ | H | 2-methyl-4-methyl-6-(OCH₂CF₃)pyrimidinyl | |
| 21 | CH₃ | H | 2-methyl-4-methyl-6-ethoxypyrimidinyl | |

TABLE 2-continued

| Example No. | R¹ | R² | R³ | Melting point (°C.) |
|---|---|---|---|---|
| 22 | CH₃ | H | pyrimidine with OC₂H₅, OC₂H₅ | |
| 23 | C₂H₅ | H | pyrimidine with Cl, OCH₃ | |
| 24 | CH₃ | H | pyrimidine with Cl, OC₂H₅ | |
| 25 | CH₃ | H | pyrimidine with CH₃, CH₃ | |

PREPARATION OF STARTING SUBSTANCES OF THE FORMULA (II)

EXAMPLE II-1

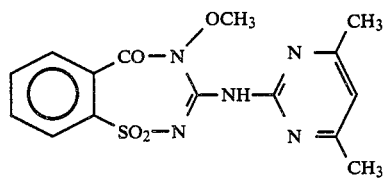

A solution of 60 g (0.25 mole) of 2-chlorosulphonyl-benzoyl chloride in 50 ml of methylene chloride is added dropwise to a mixture of 49 g (0.25 mole) of N'-(4,6-dimethylpyrimidin-2-yl)-N''-methoxyguanidine, 50 g (0.63 mole) of pyridine and 200 ml of methylene chloride at −10° C. to −5° C., with stirring. The mixture is then subsequently stirred at 20° to 25° C. for 3 hours. After washing the methylene chloride solution with dilute hydrochloric acid and ice-water and drying, filtering and concentrating, a residue is obtained which is made to crystallise by trituration with ethanol. The product thereby obtained as crystals is isolated by filtration with suction.

65 g (72% of theory) of the compound of the above-mentioned structural formula of melting point 185° C. are obtained.

The compounds of the formula (II) listed in the following Table 3 can be prepared by the process described by way of example in the preceding example II-1:

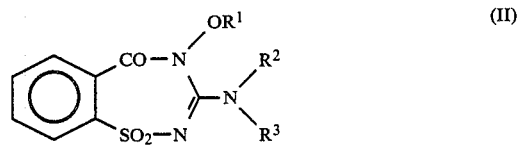

TABLE 3

| Example No. | R¹ | R² | R³ | Melting point |
|---|---|---|---|---|
| (II-2) | —CH₂—C₆H₅ | H | pyrimidine with CH₃, CH₃ | 162 |

TABLE 3-continued

| Example No. | R¹ | R² | R³ | Melting point |
|---|---|---|---|---|
| (II-3) | —C$_8$H$_{17}$ | H | 4,6-dimethylpyrimidin-2-yl | 136 |
| (II-4) | —C$_4$H$_9$ | H | 4,6-dimethylpyrimidin-2-yl | amorphous |
| (II-5) | —C$_2$H$_5$ | H | 4,6-dimethylpyrimidin-2-yl | 175 |
| (II-6) | —C$_3$H$_7$—n | H | 4,6-dimethylpyrimidin-2-yl | 81 |
| (II-7) | —C$_3$H$_7$—i | H | 4,6-dimethylpyrimidin-2-yl | 155 |
| (II-8) | —C$_4$H$_9$—i | H | 4,6-dimethylpyrimidin-2-yl | |
| (II-9) | —CH$_2$CH$_2$—C$_6$H$_5$ | H | 4,6-dimethylpyrimidin-2-yl | |
| (II-10) | —CH$_2$—CH=CH$_2$ | H | 4,6-dimethylpyrimidin-2-yl | 153–156 |
| (II-11) | —CH$_3$ | H | 4-methyl-6-methoxypyrimidin-2-yl | 166 |

TABLE 3-continued

| Example No. | R¹ | R² | R³ | Melting point |
|---|---|---|---|---|
| (II-12) | —CH₃ | H | 4,6-dimethoxypyrimidin-2-yl | 180 |
| (II-13) | —CHCH₂CH₃ with CH₃ branch | H | 4,6-dimethoxypyrimidin-2-yl | |
| (II-14) | —CH₃ | H | 4-methyl-6-(difluoromethoxy)pyrimidin-2-yl | |
| (II-15) | —CH₃ | H | 4-methylpyrimidin-2-yl | 173 |
| (II-16) | —CH₂—C₆H₅ | H | 4-methylpyrimidin-2-yl | |
| (II-17) | —CH₃ | H | 4-ethylpyrimidin-2-yl | |
| (II-18) | —CH₃ | H | pyrimidin-2-yl | 110 |
| (II-19) | —C₂H₅ | H | 4-methyl-6-methoxypyrimidin-2-yl | |
| (II-20) | —C₂H₅ | H | 4,6-dimethoxypyrimidin-2-yl | |

TABLE 3-continued

| Example No. | R¹ | R² | R³ | Melting point |
|---|---|---|---|---|
| (II-21) | —CH₂—C₆H₅ | H | pyrimidine with OCH₃, OCH₃ | |
| (II-22) | —CH₂COOC₂H₅ | H | pyrimidine with OCH₃, OCH₃ | |
| (II-23) | —CH₃ | H | pyrimidine with CH₃, OC₂H₅ | |
| (II-24) | —CH₃ | H | pyrimidine with OC₂H₅, OC₂H₅ | |
| (II-25) | —CH₃ | H | pyrimidine with CH₃, OCH₂CF₃ | |
| (II-26) | —CH₂—CH=CH₂ | H | pyrimidine with CH₃, OCH₃ | |

PREPARATION OF THE STARTING SUBSTANCES OF THE FORMULA (IV)

EXAMPLE (IV-1)

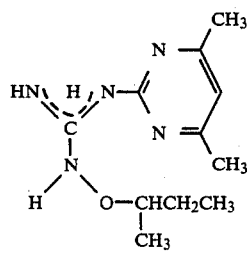

A mixture of 143 g (0.97 mole) of 2-cyanoamino-4,6-dimethyl-pyrimidine, 94.3 g (1.06 mole) of O-sec.-butyl-hydroxylamine and 190 ml of ethanol is heated at the boiling point under reflux for 6 hours. The mixture is then filtered with suction, the filtrate is concentrated and 500 ml of water are added to the residue. The product thereby obtained as crystals is isolated by filtration with suction.

131 g (57% of theory) of N'-(4,6-dimethyl-pyrimidin-2-yl)-N"-sec.-butoxy-guanidine of melting point 78° C. are obtained.

The compounds of the formula (IV) listed in the following Table 4 can be prepared analogously:

TABLE 4

| Example No. | R¹ | R² | R³ | Melting point (°C.) |
|---|---|---|---|---|
| (IV-2) | —CH₂CH(CH₃)₂ | H | 4,6-dimethylpyrimidin-2-yl | 52 |
| (IV-3) | —CH₂CH=CH₂ | H | 4,6-dimethylpyrimidin-2-yl | 103 |
| (IV-4) | —CH(CH₃)₂ | H | 4,6-dimethylpyrimidin-2-yl | |
| (IV-5) | —CH₂—C₆H₅ (benzyl) | H | 4,6-dimethylpyrimidin-2-yl | $n_D^{24} = 1.5776$ |
| (IV-6) | —C₄H₉(n) | H | 4,6-dimethylpyrimidin-2-yl | $n_D^{20} = 1.5513$ |
| (IV-7) | —C₈H₁₇(n) | H | 4,6-dimethylpyrimidin-2-yl | 58 |
| (IV-8) | —CH₂—(2-chlorophenyl) | H | 4,6-dimethylpyrimidin-2-yl | 102–103 |
| (IV-9) | —CH₂CH₂CH₂Cl | H | 4,6-dimethylpyrimidin-2-yl | 137 |

TABLE 4-continued
| Example No. | R¹ | R² | R³ | Melting point (°C.) |
|---|---|---|---|---|
| (IV-10) |  | H | 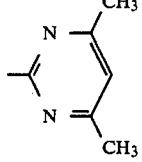 | 189–192 (Decomposition) |
| (IV-11) | —CH₂COOCH₃ | H | 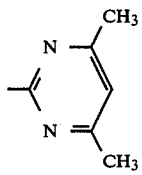 | 148–149 |
| (IV-12) | —CH₂COOC₂H₅ | H | 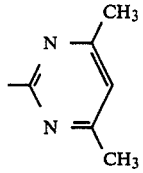 | 98–99 |
| (IV-13) | —CH(CH₃)—COOCH₃ | H | 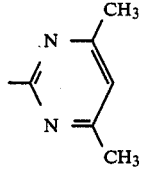 | 147–148 |
| (IV-14) | 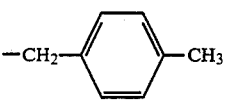 | H | 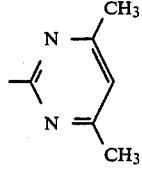 | 85–86 |
| (IV-15) | 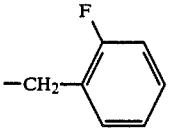 | H | 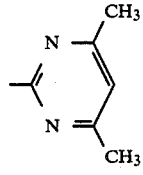 | 114–116 |
| (IV-16) |  | H | 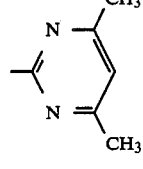 | |
| (IV-17) | 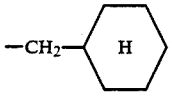 | H | 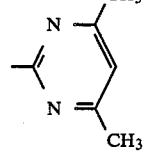 | |

TABLE 4-continued
| Example No. | R¹ | R² | R³ | Melting point (°C.) |
|---|---|---|---|---|
| (IV-18) | —CH$_2$CON(CH$_3$)$_2$ | H | 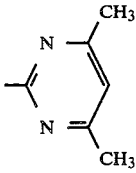 | |
| (IV-19) | —CH$_2$OCH$_3$ | H | 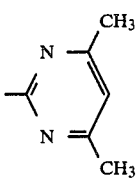 | |
| (IV-20) | —CH$_2$SCH$_3$ | H | 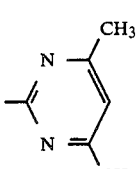 | |
| (IV-21) | 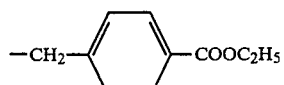 | H | 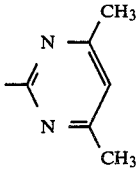 | 138 |
| (IV-22) | —CH$_2$CF$_3$ | H | 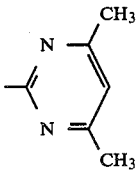 | |
| (IV-23) | 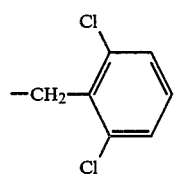 | H | 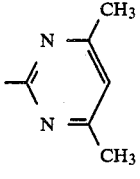 | 152 |
| (IV-24) | 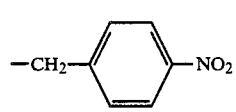 | H | 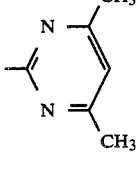 | 170–2 |
| (IV-25) | —CH$_3$ | H | 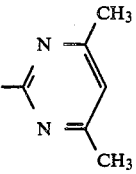 | 134–136 |

TABLE 4-continued

| Example No. | R¹ | R² | R³ | Melting point (°C.) |
|---|---|---|---|---|
| (IV-26) | —C₂H₅ | H | 2-methyl-4,6-dimethylpyrimidin-5-yl | 66 |
| (IV-27) | —CH₂—C₆H₅ | H | 2-methyl-4,6-dimethylpyrimidin-5-yl | 102 |
| (IV-28) | —CH₃ | CH₃ | 2-methyl-4,6-dimethylpyrimidin-5-yl | 95 |
| (IV-29) | CH₃ | CH₃ | 2-methyl-4,6-dimethoxypyrimidin-5-yl | 135 |
| (IV-30) | CH₃ | H | 2-methyl-4,6-dimethoxypyrimidin-5-yl | 122 |
| (IV-31) | CH₃ | H | 2-methyl-4-methylpyrimidin-5-yl | 152 |
| (IV-32) | CH₃ | H | 2-methyl-4-methoxy-6-methylpyrimidin-5-yl | 126 |
| (IV-33) | CH₃ | H | 2-methyl-4-methoxy-6-(diethylamino)-1,3,5-triazin-5-yl | 112 |
| (IV-34) | CH₃ | H | 2-methyl-4-methylthio-6-(ethylamino)-1,3,5-triazin-5-yl | 117 |

TABLE 4-continued

| Example No. | R¹ | R² | R³ | Melting point (°C.) |
|---|---|---|---|---|
| (IV-35) | $C_2H_5$ | H | 4-ethyl-2-pyrimidinyl | |
| (IV-36) | $CH_3$ | H | 4-ethyl-2-pyrimidinyl | 98 |
| (IV-37) | $-CH_2$-phenyl | H | 4-methyl-2-pyrimidinyl | 150 |
| (IV-38) | $-CH_2$-(2-chlorophenyl) | H | 4-methyl-2-pyrimidinyl | 140 |
| (IV-39) | $CH_3$ | $CH_3$ | 4-methoxy-6-methyl-2-pyrimidinyl | 135 |
| (IV-40) | $CH_3$ | H | 4-methyl-6-difluoromethoxy-2-pyrimidinyl | |
| (IV-41) | $CH_3$ | H | 4-methyl-6-ethoxy-2-pyrimidinyl | |
| (IV-42) | $-CHCH_2CH_3$<br>$\phantom{-}CH_3$ | H | 4,6-dimethoxy-2-pyrimidinyl | 68 |
| (IV-43) | $-CH_2CH(CH_3)_2$ | H | 4,6-dimethoxy-2-pyrimidinyl | 76 |

TABLE 4-continued

| Example No. | R¹ | R² | R³ | Melting point (°C.) |
|---|---|---|---|---|
| (IV-44) | —C₂H₅ | H | 2-methyl-4-methylpyrimidin-6-yl | 95 |
| (IV-45) | —CH₂—COOC₂H₅ | H | 2-methyl-4-methylpyrimidin-6-yl | |
| (IV-46) | CH(C₆H₅)₂ | H | 2,6-dimethylpyrimidin-4-yl | 165 |
| (IV-47) | CH₃ | H | 4-methoxy-6-chloropyrimidin-2-yl | 112 |
| (IV-48) | —CH₂—C₆H₅ | H | 4,6-dimethoxypyrimidin-2-yl | 74 |
| (IV-49) | —CH₃ | H | 2-methylpyrimidin-4-yl | 107–109 |
| (IV-50) | —CH₃ | H | 4,6-diethoxypyrimidin-2-yl | |
| (IV-51) | —CH₂—C₆H₅ | H | 2-methyl-4-methyl-6-methoxypyrimidine | $n_D^{20}$: 1.5645 |
| (IV-52) | —CH₂—C₆H₅ | H | 2-methyl-4-ethylpyrimidin-6-yl | 112 |
| (IV-53) | 2-fluorobenzyl | H | 2-methyl-4-methylpyrimidin-6-yl | 205 |

TABLE 4-continued

| Example No. | R¹ | R² | R³ | Melting point (°C.) |
|---|---|---|---|---|
| (IV-54) | —CH₂—CH₂—CH₂—Cl | H | 4-methylpyrimidin-5-yl | ≈102 |
| (IV-55) | —CH₂—C₆H₅ | H | 4-methyl-5-(ethoxycarbonyl)pyrimidin-2-yl | 130 |
| (IV-56) | —CH₂—CH₂—OCH₃ | H | 4-methylpyrimidin-5-yl | 242 (Decomposition) |
| (IV-57) | —CH₂—CH=CH₂ | H | 4-methyl-5-(ethoxycarbonyl)pyrimidin-2-yl | 143 |
| (IV-58) | —C₂H₅ | H | 4-ethylpyrimidin-5-yl | 83 |
| (IV-59) | —CH₃ | H | 3,5-dimethyl-1,2,4-triazin-6-yl | 143 |
| (IV-60) | —CH₃ | H | 3,5-dimethyl-1,2,4-triazin-6-yl | 126 |
| (IV-61) | —CH₃ | H | 3-methoxy-5-methyl-1,2,4-triazin-6-yl | 95 |
| (IV-62) | —CH₂—C₆H₅ | H | 3-methoxy-5-methyl-1,2,4-triazin-6-yl | 112 |

TABLE 4-continued

| Example No. | R¹ | R² | R³ | Melting point (°C.) |
|---|---|---|---|---|
| (IV-63) | —CH₂—CH₂—CH₂—CH₂—Cl | H | (4,6-dimethylpyrimidin-2-yl) | amorphous |
| (IV-64) | —CH₂—CH₂—Cl | H | (4,6-dimethylpyrimidin-2-yl) | amorphous |
| (IV-65) | —CH₂—COO CH(CH₃)₂ | H | (4,6-dimethylpyrimidin-2-yl) | 112 |
| (IV-66) | —CH₂—C₆H₅ | H | (4-SCH₃-6-NHC₂H₅-pyrimidin-2-yl) | 122 |
| (IV-67) | —CH(—C₆H₅)₂ | H | (4,6-dimethylpyrimidin-2-yl) | 147–148 |

PREPARATION OF THE STARTING SUBSTANCE OF THE FORMULA (V)

EXAMPLE V-1

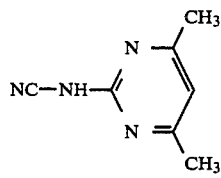

(V-1)

A mixture of 42 g (0.5 mole) of cyanoguanidine ("dicyandiamide") and 50 g (0.5 mole) of 2,4-pentanedione ("acetylacetone") is heated at 120° C. for 15 hours. After the reaction mixture has cooled, 500 ml of water are added and the solution is acidified with hydrochloric acid at 0° C. to 10° C. The product thereby obtained as crystals is isolated by filtration with suction. 51.8 g (70% of theory) of 2-cyanoamino-4,6-dimethyl-pyrimidine of melting point 205° C. are obtained.

EXAMPLE V-2

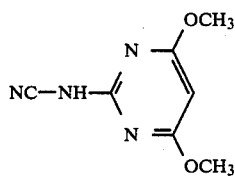

(V-2)

A solution, heated at 100° C., of 24 g (0.427 mole) of potassium hydroxide in 100 ml of water is added to a mixture of 9.2 g (0.043 mole) of 4,6-dimethoxypyrimidin-2-yl-thiourea and 70 ml of water at 100° C., with stirring. The mixture is subsequently stirred at 100° C. for 2 minutes and a solution, warmed to 100° C., of 16.2 g (0.05 mole) of lead-II acetate in 30 ml of water is then added. The mixture is heated under reflux for a further 5 minutes and is then cooled to 0° C. to 5° C., and 30 ml of glacial acetic acid are added to the aqueous solution. The product thereby obtained as crystals is isolated by filtration with suction.

6.3 g (81.5% of theory) of 2-cyanoamino-4,6-dimethoxy-pyrimidine of melting point 202° C. are obtained.

The compounds of the formula (V) listed in the following Table 5 can be prepared by the process described by way of example in the preceding example:

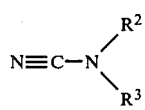

TABLE 5

| Example No. | R² | R³ | Melting point (°C.) |
|---|---|---|---|
| (V-3) | H | pyrimidine with H and CH₃ | 203 (Decomposition) |
| (V-4) | H | pyrimidine with OCH₃ and CH₃ | 258 |
| (V-5) | H | triazine with OCH₃ and N(C₂H₅)₂ | 114 |
| (V-6) | H | triazine with SCH₃ and NHC₂H₅ | — |
| (V-7) | H | pyridine with CH₃ and CH₃ | 221 (Decomposition) |
| (V-8) | H | triazine with OCH₃ and NH—CH₃ | 210 |
| (V-9) | H | pyrimidine with OC₂H₅ and CH₃ | — |
| (V-10) | H | pyrimidine with SCH₃ and CH₃ | — |

TABLE 5-continued
| Example No. | R² | R³ | Melting point (°C.) |
|---|---|---|---|
| (V-11) | H | 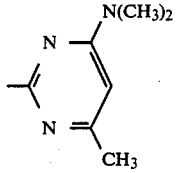 | |
| (V-12) | H | 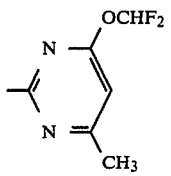 | 174 |
| (V-13) | H | 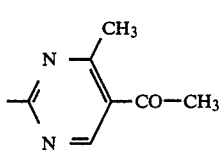 | 174 |
| (V-14) | H | 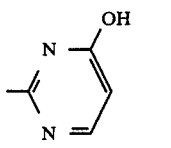 | >300 |
| (V-15) | H | 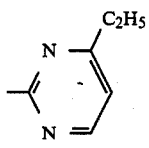 | 146 |
| (V-16) | H | 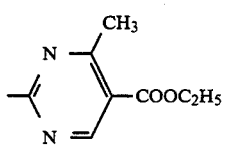 | 126 |
| (V-17) | H | 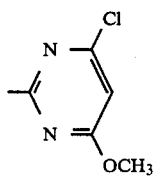 | 200 |
| (V-18) | H | 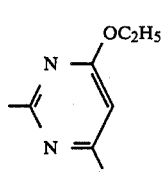 | 235–237 |
| (V-19) | H | 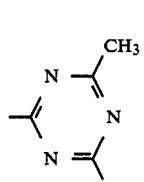 | 234 |

TABLE 5-continued

| Example No. | R² | R³ | Melting point (°C.) |
|---|---|---|---|
| (V-20) | H | 2-methyl-4-chloro-6-ethoxypyrimidin-5-yl | |
| (V-21) | H | 2-methyl-4-methylpyridin-3-yl | 247–250 |
| (V-22) | H | 2-methylpyrimidin-5-yl | 186 |
| (V-23) | H | 2-methyl-4-chloro-6-dimethylaminopyrimidin-5-yl | |
| (V-24) | H | 2,4-dimethyl-5-acetylpyrimidin-? | 174 |
| (V-25) | —CH₂—C₆H₅ | 2,4,6-trimethylpyrimidin-5-yl | 67–68 |
| (V-26) | H | 2-methyl-4-hydroxy-5-ethoxycarbonylpyrimidin-? | 220 (decomp.) |
| (V-27) | H | 2-methyl-4,6-dimethoxy-1,3,5-triazin-? | >300 |
| (V-28) | H | 2-methyl-4-methoxy-6-methyl-1,3,5-triazin-? | 183 |

TABLE 5-continued

| Example No. | R² | R³ | Melting point (°C.) |
|---|---|---|---|
| (V-29) | H | 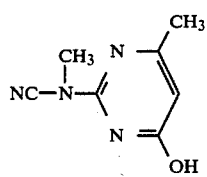 | >200° (decomp.) |
| (V-30) | H | | 132 |

2-(Alkyl-cyano-amino)-pyrimidines of the formula (V) can be prepared, for example, as follows:

EXAMPLE (V-31)

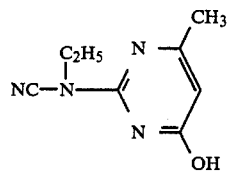

12.6 g (0.1 mole) of dimethylsulphate are added dropwise to a solution of 15 g (0.1 mole) of 2-cyanoamino-4-hydroxy-6-methyl-pyrimidine and 4.1 g (0.1 mole) of sodium hydroxide in 60 ml of water, whereupon the reaction temperature rises from 20° C. to 40° C. After the mixture has been stirred at 20° C. for two hours, the product obtained as crystals is isolated by filtration with suction.

11.1 g (68% of theory) of 2-(methyl-cyano-amino)-4-hydroxy-6-methyl-pyrimidine of melting point 290° C. are obtained.

The following compound is obtained analogously:

EXAMPLE (V-32)

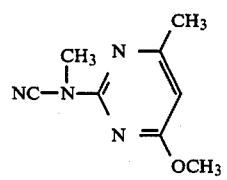

Melting point: 215° C. to 220° C.

EXAMPLE (V-33)

127.5 g (1 mole) of dimethyl sulphate are added dropwise to a solution of 75 g (0.5 mole) of 2-cyano-amino-4-hydroxy-6-methyl-pyrimidine—prepared according to process (b)—and 44 g (1.1 mole) of sodium hydroxide in 750 ml of water, whereupon the reaction temperature rises from 20° C. to 35° C. After the mixture has been stirred at 20° C. for twelve hours, it is brought to a pH value of between 9 and 10 by addition of sodium hydroxide solution and the product obtained as crystals is isolated by filtration with suction.

13 g (15% of theory) of 2-(methyl-cyano-amino)-4-methoxy-6-methyl-pyrimidine of melting point 123° C. are obtained.

The following compounds are obtained analogously:

EXAMPLE (V-34)

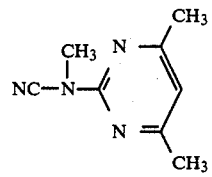

Melting point: 104° C.

EXAMPLE (V-35)

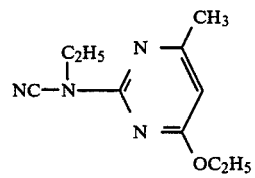

Melting point: 71° C.

PREPARATION OF THE STARTING SUBSTANCES OF THE FORMULA (XI)

EXAMPLE (XI-1)

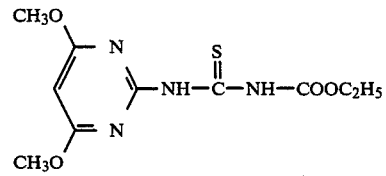

A mixture of 15.5 g (0.1 mole) of 2-amino-4,6-dimethoxy-pyrimidine, 13.1 g (0.1 mole) of ethoxycarbonyl isothiocyanate and 200 ml of acetonitrile is stirred at 60°

C. for 2 hours. It is then cooled to 10° C. and the product obtained as crystals is isolated by filtration with suction.

22.5 g (79% of theory) of 1-(ethoxycarbonyl)-3-(4,6-dimethoxy-pyrimidin-2-yl)-thiourea of melting point 194° C. (decomposition) are obtained.

The compounds of the formula (XI). listed in the following Table 6 can be prepared by the process described by way of example in the preceding example:

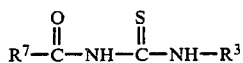
(XI)

TABLE 6

| Example No. | $R^7$ | $R^3$ | Melting point (°C.) |
|---|---|---|---|
| (XI-2) | phenyl | 4,6-dimethoxy-pyrimidin-2-yl (OCH$_3$, OCH$_3$) | 189 |
| (XI-3) | phenyl | 4-methyl-pyrimidin-2-yl (CH$_3$) | 198–9 (decomp.) |
| (XI-4) | —OC$_2$H$_5$ | 4-methyl-6-methoxy-pyrimidin-2-yl (CH$_3$, OCH$_3$) | 217 |
| (XI-5) | phenyl | 4-methyl-6-methoxy-pyrimidin-2-yl (CH$_3$, OCH$_3$) | 190 |
| (XI-6) | —OC$_2$H$_5$ | 4,6-dimethyl-pyridin-2-yl (CH$_3$, CH$_3$) | 140 |
| (XI-7) | phenyl | 4,6-dimethyl-pyridin-2-yl (CH$_3$, CH$_3$) | 145 |
| (XI-8) | phenyl | 4-difluoromethoxy-6-methyl-pyrimidin-2-yl (OCHF$_2$, CH$_3$) | 182 |
| (XI-9) | —OC$_2$H$_5$ | 4,6-bis(difluoromethoxy)-pyrimidin-2-yl (OCHF$_2$, OCHF$_2$) | 173 |
| (XI-10) | —OC$_2$H$_5$ | 4-chloro-6-dimethylamino-pyrimidin-2-yl (Cl, N(CH$_3$)$_2$) | 168 |
| (XI-11) | —OC$_2$H$_5$ | 4-methyl-6-difluoromethoxy-pyrimidin-2-yl (CH$_3$, OCHF$_2$) | 184–185 |
| (XI-12) | —OC$_2$H$_5$ | 4-chloro-6-methoxy-pyrimidin-2-yl (Cl, OCH$_3$) | 160–162 |
| (XI-13) | —OC$_2$H$_5$ | 4-methyl-6-ethoxy-pyrimidin-2-yl (CH$_3$, OC$_2$H$_5$) | |
| (XI-14) | —OC$_2$H$_5$ | 4-methyl-6-methylthio-pyrimidin-2-yl (CH$_3$, SCH$_3$) | |
| (XI-15) | —OC$_2$H$_5$ | 4-methyl-6-dimethylamino-pyrimidin-2-yl (CH$_3$, N(CH$_3$)$_2$) | |
| (XI-16) | phenyl | pyrimidin-2-yl | 173 |
| (XI-17) | phenyl | 4,6-diethoxy-pyrimidin-2-yl (OC$_2$H$_5$, OC$_2$H$_5$) | 179 |

TABLE 6-continued

| Example No. | R⁷ | R³ | Melting point (°C.) |
|---|---|---|---|
| (XI-18) | —OC₂H₅ | 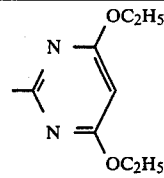 | 159 |
| (XI-19) | 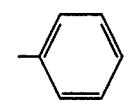 | 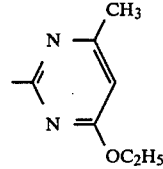 | 156 |
| (XI-20) | —OC₂H₅ | 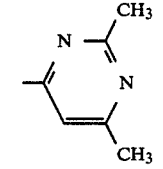 | 169 |
| (XI-21) | 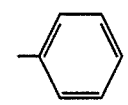 | 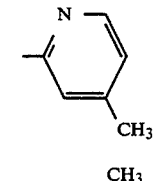 | 161 |
| (XI-22) | —OC₂H₅ | 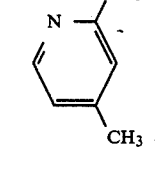 | 118–119 |
| (XI-23) | 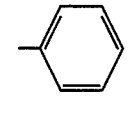 | 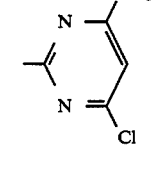 | 144 |
| (XI-24) | —OC₂H₅ | 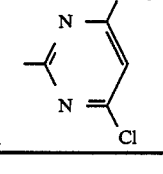 | 122–124 |

PREPARATION OF STARTING SUBSTANCES OF THE FORMULA (XII)

EXAMPLE (XII-1)

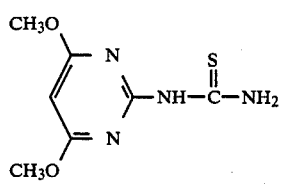

A mixture of 5.0 g (0.0175 mole) of 1-(ethoxycarbonyl)-3-(4,6-dimethoxy-pyrimidin-2-yl)-thiourea, 4.0 g (0.1 mole) of sodium hydroxide and 100 ml of water is stirred at 20° C. for 2 days. Dilute hydrochloric acid is then added dropwise, with stirring, until the solution has been rendered acid and the evolution of $CO_2$ has ended. The product obtained as crystals is isolated by filtration with suction.

3.5 g (94% of theory) of 4,6-dimethoxy-pyrimidin-2-yl-thiourea of melting point 245°–8° C. (decomposition) are obtained.

The compounds of the formula (XII) listed in the following Table 7 can be prepared by the process described by way of example in the preceding example:

TABLE 7

| Example No. | R³ | Melting point (°C.) |
|---|---|---|
| (XII-2) | 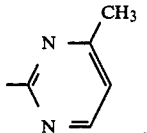 | 264–265 |
| (XII-3) | 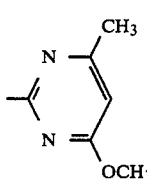 | 207 |
| (XII-4) | 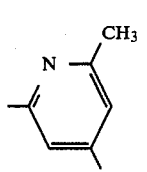 | 260 |
| (XII-5) | 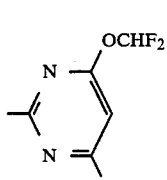 | 194 |
| (XII-6) | 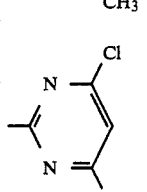 | 225–227 |
| (XII-7) | 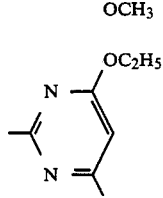 | |

TABLE 7-continued

| Example No. | R³ | Melting point (°C.) |
|---|---|---|
| (XII-8) | N-pyrimidinyl | 263 |
| (XII-9) | pyrimidinyl with OC₂H₅, OC₂H₅ | 166 |
| (XII-10) | pyrimidinyl with CH₃, N(CH₃)₂ | |
| (XII-11) | pyrimidinyl with CH₃, SCH₃ | |
| (XII-12) | pyrimidinyl with CH₃, Cl | >180 (decomp.) |

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example, the following compounds of preparation examples (1) and (2) showed a better herbicidal activity than the compound (A) known from the prior art.

EXAMPLE B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test the following compounds of preparation examples (1) and (2) showed a better herbicidal activity than the compounds (A) known from the prior art.

We claim:

1. A 1-(2-oxyaminocarbonylphenylsulphonyl)-3-heteroaryl-urea of the formula

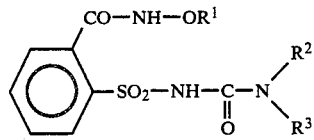

in which

R¹ is $C_1$-$C_{12}$-alkyl (which is optionally substituted by fluorine, chlorine, cyano, $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-alkyl-carbonyl, $C_1$-$C_4$-alkoxy-carbonyl, $C_1$-$C_4$-alkylamino-carbonyl or di-$C_1$-$C_4$-alkyl-amino-carbonyl, or is $C_3$-$C_6$-alkenyl (which is optionally substituted by fluorine, chlorine or bromine), $C_3$-$C_6$-alkinyl, $C_3$-$C_6$-cycloalkyl, $C_3$-$C_6$-cycloalkyl-$C_1$-$C_2$-alkyl or phenyl-$C_1$-$C_2$-alkyl, (which is optionally substituted by fluorine, chlorine, nitro, cyano, $C_1$-$C_4$-alkyl, $C_1$-$C_4$-alkoxy or $C_1$-$C_4$-alkoxycarbonyl), or is benzhydryl, or is phenyl (which is optionally substituted by fluorine, chlorine, nitro, cyano, $C_1$-$C_4$-alkyl, trifluoromethyl, $C_1$-$C_4$-alkoxy, $C_1$-$C_2$-fluoroalkoxy, $C_1$-$C_4$-alkylthio, trifluoromethylthio or $C_1$-$C_4$-alkkoxycarbonyl), R₂ is hydrogen or $C_1$-$C_4$-alkyl (which is optionally substituted by fluorine, chlorine, cyano, $C_1$-$C_4$-alkoxy-carbonyl), and R₃ is a pyrimidin-2-yl radical optionally substituted in 4- and/or 6-position by fluorine, chlorine, bromine, hydroxyl, $C_1$-$C_4$-alkyl (which is optionally substituted by fluorine and/or chlorine), $C_1$-$C_4$-alkylthio (which is optionally substituted by fluorine and/or chlorine), amino, $C_1$-$C_4$-alkylamino or di-($C_1$-$C_4$-alkyl)-amino, and which is optionally substituted in 5-position by fluorine, chlorine, bromine, cyano, formyl or $C_1$-$C_4$-alkyl (which is optionally substituted by fluorine and/or chlorine), or by $C_1$-$C_4$-alkyl-carbonyl or $C_1$-$C_4$-alkoxy-carbonyl.

2. A urea according to claim 1; in which $R^1$ is $C_1$-$C_8$-alkyl (which is optionally substituted by fluorine or chlorine), $C_3$-$C_4$-alkenyl, $C_1$-$C_2$-alkoxy-carbonylmethyl, phenyl, phenethyl or benzyl (which is optionally substituted by fluorine, chlorine, nitro, cyano, methyl, methoxy or methoxy-carbonyl), $R^2$ is hydrogen, and $R^3$ is pyrimidin-2-yl substituted in the 4-position by chlorine, methyl, ethyl, methoxy, difluoromethoxy or ethoxy, and optionally substituted in the 6-position by chlorine, methyl, methoxy, ethoxy, methylthio, ethylthio, dimethylamino or diethylamino.

3. A urea according to claim 2, wherein such compound is 1-(2-methoxyaminocarbonylphenylsulphonyl)-3-(4,6-dimethylpyrimidin-2-yl)-urea of the formula

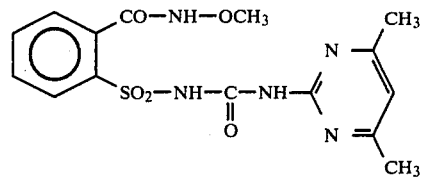

4. A herbicidal composition comprising a herbicidally effective amount of a urea according to claim 1 in admixture with a diluent.

5. A method of combating unwanted vegetation which comprises applying to such vegetation or to a locus from which it is desired to exclude such vegetation a herbicidally effective amount of a urea according to claim 1.

6. A method of combating unwanted vegetation which comprises applying to such vegetation or to a locus from which it is desired to exclude such vegetation a herbicidally effective amount of a urea according to claim 3.

* * * * *

UNITED STATES PATENT AND TRADEMARK OFFICE
CERTIFICATE OF CORRECTION

PATENT NO. : 4,704,158

DATED : November 3, 1987

INVENTOR(S) : Hans-Joachim Diehr, et al.

It is certified that error appears in the above-identified patent and that said Letters Patent is hereby corrected as shown below:

Title Page, under "Foreign Application Priority Data, line 1    Delete "3531927" and substitute --3431927--

Col. 9, line 20    Delete "dicyanidiamide" and substitute --dicyandiamide--

Col. 9, line 58    Delete "K7" and substitute --$R^7$--

Col. 11, line 24   Delete "Galibsoga" and substitute --Galinsoga--

Col. 11, line 56   Delete "lantations" and substitute --plantations--

Col. 11, line 58   Delete "annula" and substitute --annual--

Col. 12, line 58   Delete "mixture" and substitute --mixtures--

Signed and Sealed this

Third Day of May, 1988

Attest:

DONALD J. QUIGG

Attesting Officer

Commissioner of Patents and Trademarks